United States Patent
Rimm et al.

(10) Patent No.: US 6,670,197 B2
(45) Date of Patent: Dec. 30, 2003

(54) METHOD FOR ASSAYING WHOLE BLOOD FOR THE PRESENCE OR ABSENCE OF CIRCULATING CANCER OR OTHER TARGET CELL FRAGMENTS

(76) Inventors: David L. Rimm, 15 Pawson Landing, Branford, CT (US) 06405; Stephen C. Wardlaw, High Rock, Lyme, CT (US) 06371; Robert A. Levine, 31 Pilgrim La., Guilford, CT (US) 06437; Paul Fiedler, 90 Gilnock Dr., New Haven, CT (US) 06515

( * ) Notice: Subject to any disclaimer, the term of this patent is extended or adjusted under 35 U.S.C. 154(b) by 487 days.

(21) Appl. No.: 09/800,344

(22) Filed: Mar. 5, 2001

(65) Prior Publication Data

US 2001/0024802 A1 Sep. 27, 2001

Related U.S. Application Data

(63) Continuation-in-part of application No. 08/976,886, filed on Nov. 24, 1997, now Pat. No. 6,197,523.

(51) Int. Cl.$^7$ ............................................. G01N 33/543
(52) U.S. Cl. ........................ 436/518; 356/36; 435/7.1; 435/7.22; 435/7.23; 435/7.24; 436/63; 436/64; 436/523
(58) Field of Search .............................. 435/7.22, 7.23, 435/7.24, 7.1; 436/63, 64, 523, 518; 356/36

(56) References Cited

U.S. PATENT DOCUMENTS

| | | | | |
|---|---|---|---|---|
| 5,252,460 A | * | 10/1993 | Fiedler et al. | 435/7.22 |
| 5,403,714 A | * | 4/1995 | Levine et al. | 435/7.2 |
| 5,496,704 A | * | 3/1996 | Fiedler et al. | 435/7.22 |
| 5,635,362 A | * | 6/1997 | Levine et al. | 435/7.24 |
| 5,759,794 A | * | 6/1998 | Levine et al. | 435/7.24 |
| 5,776,710 A | * | 7/1998 | Levine et al. | 435/7.24 |
| 5,834,217 A | * | 11/1998 | Levine et al. | 435/7.24 |
| 6,444,436 B1 | * | 9/2002 | Rimm et al. | 435/40.51 |

* cited by examiner

*Primary Examiner*—Christopher L. Chin
(74) *Attorney, Agent, or Firm*—William W. Jones

(57) ABSTRACT

This method for analyzing blood enables one to isolate, detect, enumerate and confirm under magnification the presence or absence of fragments of target analyte cancer cells which are circulating in blood. The analysis is performed in a sample of centrifuged anticoagulated whole blood. The analysis of the presence or absence of fragments of cancer cells relies on the detection of external or internal binding sites which are known to be present only in or on tumorous cancer cells. Fluorophors with distinct wavelength emissions are coupled with antibodies, or other binding moieties such as complementary nucleotide sequences, which antibodies are directed against the epithelial cell fragment membrane binding sites, such as internal or external surface epitopes on the cell fragments, or internal binding sites on cell organelles; and which nucleotide sequences are complementary to portions of cell fragment RNA and/or DNA. The labled binding agents are humoric or soluble in the blood sample. The labeled fluorometric binding site-specific materials may be coupled to small plastic beads which have a density or specific gravity that is preferably greater than the specific gravity or density of the red blood cells. The target cell fragments are less dense than the red cells, and typically have the same density or specific gravity as the platelets or white blood cells in the blood sample. Any of the labeled beads which couple with target cell analyte fragments will have a density or specific gravity that is less than the red cells in the blood sample. Thus cell fragment/labeled bead couples will gravitate into an area in the centrifuged blood sample which area is somewhere above the centrifuged red cell layer. The detection of the labeled target analyte/particle couples can be performed in situ in the centrifuged blood sample either visually or photometrically.

1 Claim, No Drawings

METHOD FOR ASSAYING WHOLE BLOOD FOR THE PRESENCE OR ABSENCE OF CIRCULATING CANCER OR OTHER TARGET CELL FRAGMENTS

This is a continuation-in-part of co-pending U.S. Ser. No. 08/976,886, filed Nov. 24, 1997, now U.S. Pat. No. 6,197,523, the contents of which are incorporated herein in their entirety.

TECHNICAL FIELD

This invention relates to a method and assembly for assaying an anticoagulated whole blood sample for the presence or absence of circulating fragments of cancer cells or fragments of other target cells. The blood sample is contained in a transparent sampling container assembly and the assay can be performed in situ in the sampling tube assembly. More particularly, the method of this invention involves the centrifugal density-based separation of the contents of the blood sample in a manner which will ensure that any circulating target cell fragments in the blood sample are physically displaced by their density into a predetermined axial location in the blood sample and in the sampling container assembly, and also into a restricted optical plane in the sampling container assembly which is adjacent to the wall of the sampling container, and finally into a very well-defined zone of that optical plane.

BACKGROUND ART

Cytology is the science and technology involved in the morphological characterization of mammalian cells. Cytology has clinical utility in both human and veterinary medicine. Cytology is most often used to diagnose the presence or absence of malignancy in exfoliated or harvested cells: a) that are shed into a body cavity such as the pleural space or peritoneum; b) that are shed into a body fluid that is excreted as, for example, sputum or urine; c) that are obtained by scraping or brushing a body surface, such as the uterine cervix, the uterine cavity, or bronchial mucosa; or d) that are obtained by direct needle-mediated aspiration from a tumor such as tumors of the thyroid, breast, lung, or the like. The exfoliated or harvested cells are then typically fixed, stained and visually studied, usually by bright field microscopy, and then, if needed, by immunologic stains and/or other molecular techniques.

This year approximately five hundred sixty thousand people will die from solid tumors (predominantly carcinomas) in the USA. Many of these deaths could be prevented by early diagnosis of these malignancies. Unfortunately, with the possible exception of the Prostate Specific Antigen (PSA) test for prostate cancer, there is no practical and routine methods that have been found to be effective for early detection of solid tumors through blood analysis.

Through early detection of cervical cancer, the Pap smear has decreased mortality from cervical cancer in the United States by over seventy percent. Development of an analogous test for other solid tumors could have a similar impact on overall cancer mortality.

The presence of circulating cancer cells that are spontaneously shed by cancerous tumors into the circulating blood stream which is supplying the tumors with oxygen and nutrients has been confirmed. The presence of such cells in the blood stream has been inferred for decades because of the spread of cancerous tumors by what has been described as the hematogenous route and on very rare occasions have been visualized in blood specimens. Recently sophisticated procedures which employ reverse transcriptase in conjunction with Polymerase Chain Reaction (PCR) have been able to detect the presence of tumor cells by their molecular signature in a significant number of patients with cancer, both when the cancer is localized and after it has spread.

An additional means of detecting circulating cancer cell employs a technology known as Fluorescent Activated Cell Sorting (FACS), such as that manufactured by Becton Dickinson and Company of Franklin Lakes, N.J. The FACS detection of circulating cancer cells involves detection of cancer cells by detecting fluorescent labeled antibodies which are directed against and bound to one or more epitopes that are present on or in cancer cells, and are not present on or in normal blood cells, and/or by detecting combinations of epitopes that are present on or in circulating normal blood cells and that may or may not be present on or in cancerous cells, or combinations of the aforesaid methods.

The FACS technology is thus based on cell highlighting, i.e., it is photometric and utilizes antibody-epitope specificity, and it cannot be used to morphologically analyze cells in situ in the FACS instrument. Both the reverse transcriptase/PCR, (the molecular method), and the FACS, (the immuno-phenotypic method), require that the origin of the tumor being sought be known in order to select for the specific molecular species or immuno-phenotypic signals. The aforesaid techniques have contributed to confirmation of the theory that cancer cells do circulate in the blood stream, but these techniques are not practical especially in point of care applications, by virtue of their cost and/or nature, for detecting the presence or absence of circulating tumorous cancer cells in the blood stream. Thus, there is no general or generic blood analyzing procedure for the detection and confirmation of the malignant nature of circulating cancer cells, regardless of their source, in a patient. In addition, neither the aforesaid molecular nor the immuno-phenotypic methods utilize in situ, i.e., in a closed sampling system, cytopathologically-based analyses to determine the morphometric characteristics of circulating cells which permit cancer cells to be identified and confirmed.

Since approximately eighty two percent of all cancers are epithelial in origin (seventy two percent of which are fatal), epithelial cancer cells should be detectable in circulating blood. While the presence of epithelial cells in the circulating blood stream does not, by itself, prove malignancy, it does alert the cytologist to the greater likelihood of malignancy since epithelial cells are not normally seen in the circulating blood stream. In certain cases, however; such as after surgery; or as a result of physical trauma; or as a result of dental flossing, or in cases of prostatitis, for example, it is possible that non-malignant epithelial cells may be found in the circulating blood stream. Visual morphological analysis of cells is currently the most reliable way to distinguish cancerous epithelial cells from benign epithelial cells which are found in the circulating blood sample. One problem which exists in connection with attempts to detect circulating cancer cells in blood via morphological analysis relates to the fact that circulating cancer cells in blood are often virtually indistinguishable from circulating hematologic progenitor cells, or blasts, by cytological analysis alone.

The paucity of cancer cells that may be present in a sample of circulating blood would require the cytopathologist to carefully examine approximately ten million nucleated blood cells in order to find one cancer cell, and that one cancer cell would be randomly located in the ten million nucleated blood cells, which in turn will themselves be homogeneously dispersed in a sea of five billion non-nucleated cellular blood constituents, i.e., the erythrocytes, plus two hundred fifty million platelets, all of which will be found in one milliliter of blood. Such a task would be very time consuming, and is thus impractical for use in analyzing a patient's blood for the presence or absence of cancer cells.

A technique has been developed to quantitate constituent layers in a complex material mixture by centrifuging a sample of the material mixture in a capillary tube or other container which contains an insert, typically a float. The float complements the configuration of the sample container, and is preferably cylindrical when a tubular container is used. The insert has a specific gravity which causes it to settle into the centrifuged mixture to a degree which creates a spatially restricted free volume in the container into which the layer, or layers to be measured will settle. The layers to be measured are thus physically elongated, and can thus be more easily and accurately measured. The aforesaid technique is described in U.S. Pat. Nos. 4,027,660, issued Jun. 7, 1977; 4,082,085 issued Apr. 4, 1978; 4,156,570 issued May 29, 1979; and others. This technology is presently being marketed by Becton Dickinson and Company under the registered trademark "QBC". This "QBC" technology has been adapted for use in the isolation and identification of microfilarial infestation of a blood sample, as set forth in U.S. Pat. No. 4,190,328, issued Feb. 26, 1980. U.S. Pat. Nos. 5,403,714, issued Apr. 4, 1995; 5,496,704, issued Mar. 5, 1996; 5,506,145, issued Apr. 9, 1996; and others describe the use of the aforesaid "QBC" technology to assay anticoagulated whole blood for various analytes; and also to assay tissue samples for the presence or absence of cancerous tumor cells, wherein tissue samples are admixed with a saline buffer solution prior to analysis.

Commonly owned co-pending U.S. patent applications Ser. No. 08/976,886, filed Nov. 24, 1997, and U.S. Ser. No. 09/507,635, filed Feb. 22, 2000 both relate to the detection of circulating cancer cells in a sample of anticoagulated whole blood. The methods described in these patent applications describe the detection of intact epithelial tumor cells in the blood sample, but do not suggest that circulating fragments of epithelial tumor cells could be detected in the blood sample.

While the aforesaid copending patent applications describe the detection of intact cancer cells in an anticoagulated whole blood sample, since intact cancer cells may not be present in a blood sample of an individual with cancer, there exists a need for a simple procedure, and a system for performing such a procedure, whereby a sample of capillary or venous blood could be quickly and accurately analyzed for the presence or absence of circulating fragments of cancer cells, or fragments of other target cells. Additionally, the procedure should enable one to differentiate cancer cell fragments from other cell fragments; and also enable one to confirm the nature of any detected cell fragments, all in situ, in the blood sampling paraphernalia.

DISCLOSURE OF THE INVENTION

This invention relates to a method and apparatus for visually or photometrically detecting fragments of circulating cancer or other target cells in an anticoagulated whole blood sample, which blood sample is contained in a transparent sampling container. The detection and confirmation of circulating fragments of cancer or other target cells in the blood sample can be attained in a matter of minutes by utilizing the fact that circulating cancer cell fragments, which are of epithelial origin, all possess epitopes or binding sites which are unique to epithelial cells. These epitopes or binding sites may be surface binding sites such as CAMS which are found on the target cell membrane, and therefore are also found on fragments of the target cell membrane; or the binding sites may be epitopes or nucleotide sequences which are naturally located internally in the target cells, and that are exposed to external in situ detection, only after the target cells rupture.

Intact epithelial tumor cells that are found circulating in blood have a specific gravity or density that will cause them to gravitate into the white cell/platelet, or buffy coat, area in a centrifuged sample of anticoagulated whole blood. Thus, intact epithelial cells in the blood sample can be found in a relatively well defined area in a centrifuged sample of anticoagulated whole blood. Once located in a centrifuged sample of anticoagulated whole blood, epithelial cells can be morphologically analyzed with suitable colorants, such as acridine orange, and can thus be confirmed as being of epithelial origin. The same cannot be said for fragments of epithelial cancer cells in circulating blood. Circulating epithelial cell fragments found in blood do not have the same specific gravity or density as intact epithelial cells, and cannot be morphologically identified due to the fact that, once the cells rupture, the morphological character of the cells is destroyed. One problem with locating circulating cancer cell fragments in a centrifuged sample of anticoagulated whole blood is: Where will they be found in the centrifuged blood sample? Another problem with locating circulating cancer cell fragments in a centrifuged sample of anticoagulated whole blood relates to the size of the fragments, and the ability to visually or photometrically detect them in the blood sample. Epithelial cell membranes, due to their phospholipid nature, are less dense than intact epithelial cells, and are, generally speaking less dense than platelets in the blood sample, but heavier than plasma. Thus, epithelial cell fragments would be expected to gravitate to a location between the platelet layer and the plasma layer in a centrifuged sample of anticoagulated whole blood.

This invention involves the employment of paraphernalia and a procedure for altering the specific gravity or density of ruptured epithelial-origin cancer cell fragments which are present in a sample of the circulating blood stream so as to establish a predictable location for the cell fragments in the centrifuged blood sample, and to visually and/or photometrically differentiate the cell fragments from other formed components in the centrifuged blood sample.

This invention permits the detection of particles of biologic origin, such as cell membranes and cell organelles, that because of their size and shape and rarity may not be readily morphologically detectable. The particles detected in the present invention are the cell membranes of epithelial cells that are circulating in the blood or have circulated in blood and have been disrupted. As noted above, normally the cells of epithelial origin do not circulate in the blood. When they do it is indicative of illness such as cancer of epithelial origin referred to as carcinoma, such as lung cancer or colon cancer, or an inflammation of a tissue of epithelial origin, such as prostatitis.

Abnormal cells of epithelial origin may be identified by their morphology coupled with labeled markers directed against specific or relatively specific epitopes present on the surface of these cells. These markers may be fluorescent compounds or colored, or fluorescently colored, particles or liposomes coupled to antibodies or other binding substances which are specific to the epithelial epitopes. Examples of such epitopes include CAM, and the like. Methods for accomplishing the aforementioned detection is described in U.S. Pat. Nos. 5,593,848; 5,460,979; 5,635,362; 5,496,704; 5,252,460. None of the aforementioned disclosures suggest the desirability for the detection of remnants of ruptured cells by detection of their remnants such as organelles and or cell membranes.

The detection of cell membranes of epithelial origin is not possible by morphology alone since membranes from ruptured cells of epithelial origin are not morphologically distinguishable from membranes from other cells such as leukocytes or erythrocytes. Cell membranes are, because of their phospholipid nature, less dense than intact cells and in fact when subject to centrifugal densimetric separation become localized at the plasma platelet interface. The membranes are generally heavier than plasma, i.e., greater than 1.020 gm/ml, and less dense than most platelets, i.e., less than 1.040 gm/ml. When small, about 0.5 to 2.5 micron diameter, beads having a density of 1.3 gm/ml (obtainable from Dynal Corporation) are added, to whole anticoagulated blood they will when centrifuged settle in the bottom of the blood layer since the heaviest particulate component of blood has s density of about 1.06 gm/ml. If, however, the beads are attached to binding agents directed against epitopes present on the cell membranes and allowed to complex to their target epitopes and if the average density of the bead/cell membrane complex is such that it remains less dense than the red cells and preferably but not necessarily less dense than the cellular components of the buffy coat it may be easily detected in the buffy coat area, especially with the use of a buffy coat expanding float such as that described in the QBC® patents.

The main purpose of this invention would be to screen specimens for the presence of circulating or previously circulating epithelial cells which if present would give an indication of increased likelihood of carcinoma being present. This invention does not necessarily rely upon the altering of the density of a complex biologic target-labeled cell particle by a plastic bead. The density of the biologic target in the present invention is relatively large compared to humoral or soluble binding agents and relatively small compared to the beads. When beads are used as capture mechanisms, the location of the captured and labeled cell fragments in the blood sample will depend on the density of the beads. If a centrifuged bead layer displays the label, then it will be presumed that there are target cell fragments in the bead layer. When beads are not used as a capture body, the centrifuged labeled cell fragments will gravitate to the platelet layer or the white cell layer where they can be identified by reason of the intensity of the label emissions found in those areas of the blood sample. When there are no target cell fragments in the blood sample, there will be no high intensity label areas found in the blood sample after centrifugation. This invention permits the targeting of membrane epitopes and/or RNA and/or DNA nucleotide sequences that are not exposed in intact cells.

Since many changes and variations of the disclosed embodiment of the invention may be made without departing from the inventive concept, it is not intended to limit the invention otherwise than as required by the appended claims.

What is claimed is:

1. A method for detecting the presence or absence of fragments of circulating cancer cells in an anticoagulated whole blood sample, said method comprising the steps of:
   a) providing a transparent container having a chamber containing an insert, said container and insert combining to form a well-defined zone in the container;
   b) combining the blood sample with one or more cell fragment binding site-specific labeling agents so as to differentiate any cancer cell fragments in the blood sample from other blood sample components;
   c) placing the blood sample in the container and centrifuging the blood sample in the container so as to cause any cancer cell fragments present in the blood sample to gravitate by density into said well-defined zone in the container; and
   f) examining the well-defined zone in the container to determine the presence or absence of labeled cancer cell fragments in the blood sample.

* * * * *